US012752092B2

(12) United States Patent
Bizet et al.

(10) Patent No.: US 12,752,092 B2
(45) Date of Patent: Oct. 6, 2026

(54) MICRONEEDLE APPLICATOR

(71) Applicant: APTAR FRANCE SAS, Le Neubourg (FR)

(72) Inventors: Bruno Bizet, Sancé (FR); Vincent Chamarande, Mâcon (FR)

(73) Assignee: APTAR FRANCE SAS, Le Neubourg (FR)

( * ) Notice: Subject to any disclaimer, the term of this patent is extended or adjusted under 35 U.S.C. 154(b) by 570 days.

(21) Appl. No.: 18/275,837

(22) PCT Filed: Feb. 7, 2022

(86) PCT No.: PCT/FR2022/050225
§ 371 (c)(1),
(2) Date: Aug. 4, 2023

(87) PCT Pub. No.: WO2022/171953
PCT Pub. Date: Aug. 18, 2022

(65) Prior Publication Data
US 2024/0123208 A1 Apr. 18, 2024

(30) Foreign Application Priority Data
Feb. 9, 2021 (FR) ....................................... 2101225

(51) Int. Cl.
*A61M 37/00* (2006.01)

(52) U.S. Cl.
CPC . *A61M 37/0015* (2013.01); *A61M 2037/0007* (2013.01); *A61M 2037/0023* (2013.01);
(Continued)

(58) Field of Classification Search
CPC .. A61M 2037/0023; A61M 2037/0061; A61M 37/0015; A61M 2037/0007;
(Continued)

(56) References Cited

U.S. PATENT DOCUMENTS

2007/0038181 A1* 2/2007 Melamud ........... A61B 17/3478
606/186
2013/0345638 A1 12/2013 Heidenreich et al.
(Continued)

FOREIGN PATENT DOCUMENTS

CN 111672023 A 9/2020
DE 202004010659 U1 * 10/2004 ............ A61M 37/00
(Continued)

OTHER PUBLICATIONS

International Search Report for PCT/FR2022/050225 dated Jun. 3, 2022 (PCT/ISA/210).

*Primary Examiner* — Wesley G Harris
(74) *Attorney, Agent, or Firm* — Sughrue Mion, PLLC

(57) ABSTRACT

Microneedle applicator having an application face (C11) provided with a fluid product outlet (C110) and with several microneedles (C111), a motor (M1) for making the microneedles (C111) vibrate, a reservoir (C13) connected to the fluid product outlet (C110), an actuation member (I11) for conveying the fluid product from the reservoir (C13) to the outlet (C110), and three distinct modules (M, C1, I1) axially connected to one another, namely, a motor module (M) housing the motor (M1), a cartridge module (C1) housing the reservoir (C13) and forming the application face (C11), and an intermediate module (I1) connected to the motor module (M) and to the cartridge module (C1). The intermediate module (I1; I2; I3) has the actuation member (I11) and transmission mechanism (I15) for transmitting the vibrations generated by the motor (M1) to the microneedles (C111).

15 Claims, 5 Drawing Sheets

Figure 1:
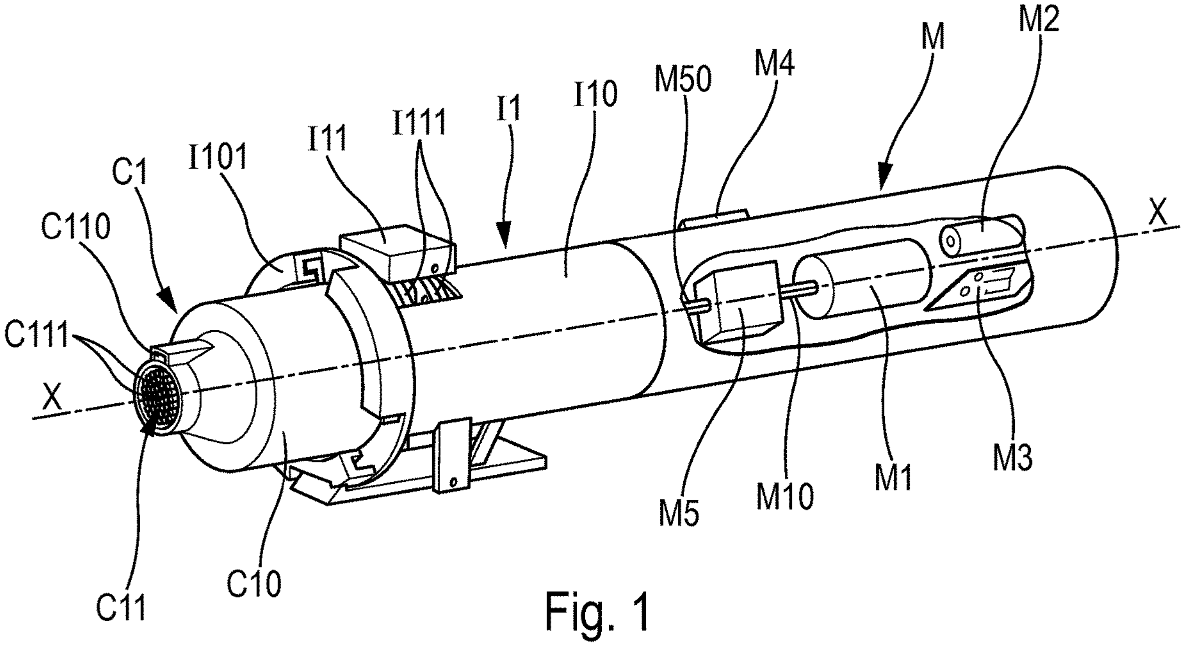

(52) U.S. Cl.
CPC ............... *A61M 2037/0046* (2013.01); *A61M 2037/0061* (2013.01); *A61M 2205/103* (2013.01); *A61M 2205/106* (2013.01)

(58) Field of Classification Search
CPC ........... A61M 2037/0046; A61M 2005/14252; A61M 2005/14506; A61M 2205/106; A61M 2205/103; A61B 2017/00398; A61B 2017/00734; A61B 2017/00761
See application file for complete search history.

(56) References Cited

U.S. PATENT DOCUMENTS

| | | | | |
|---|---|---|---|---|
| 2016/0235392 | A1 | 8/2016 | Mitragotri et al. | |
| 2017/0354810 | A1 * | 12/2017 | O'Brien, III et al. ... | A61N 1/40 |
| 2018/0280675 | A1 * | 10/2018 | Tharp ................. | A61M 35/003 |

FOREIGN PATENT DOCUMENTS

| | | | | | |
|---|---|---|---|---|---|
| KR | 20140046890 | A | * | 4/2014 | ........ A61M 37/0015 |
| KR | 10-2020-0019399 | A | | 2/2020 | |
| KR | 10-2021-0004357 | A | | 1/2021 | |
| WO | WO-2011014514 | A1 | * | 2/2011 | ........ A61M 37/0015 |

* cited by examiner

MICRONEEDLE APPLICATOR

The present invention relates to a microneedle applicator for applying a fluid product on the skin and for making it penetrate into the upper layer of the epidermis. The field of application of the invention is that of cosmetics, and not that of tattooing. The aim is to reinforce the effectiveness of a cosmetic treatment in the skin, and not to colour the skin.

Conventionally, this type of cosmetic applicator comprises an application face provided with at least one fluid product outlet and with several microneedles. A motor, often electric, is used to make the microneedles vibrate, individually or with the application face. A fluid product reservoir is connected to the fluid product outlet. The reservoir can be integrated or not to the applicator. When it is integrated, the question is thus asked about it being filled or it being replaced. The applicator can be dismountable or comprise a window for accessing the reservoir.

On the other hand, an actuation member is also provided to convey the fluid product from the fluid product reservoir to the fluid product outlet. This actuation member is often that which also controls the motor, which thus accumulates a dual function, namely, to make the microneedles vibrate and to convey the fluid product from the reservoir to the application face. The aim of the present invention is to propose a very simple applicator, just as good in terms of design and use, with a simple and intuitive fluid product distribution.

To achieve this aim, the present invention provides a microneedle applicator for applying a fluid product on the skin and for making it penetrate into the skin, the applicator defining a longitudinal axis and comprising:

- an application face provided with at least one fluid product outlet and several microneedles,
- a motor for making the microneedles vibrate,
- at least one fluid product reservoir connected to the fluid product outlet,
- an actuation member to convey the fluid product from the fluid product reservoir to the fluid product outlet, characterised in that it comprises three distinct modules axially connected to one another, namely:

- a motor module housing the motor and the accessories to make the motor function,
- a cartridge module housing the fluid product reservoir(s) and forming the application face,
- an intermediate module connected to the motor module and removably connected to the cartridge module, the intermediate module comprising the actuation member and transmission means for transmitting the vibrations generated by the motor from the motor module to the microneedles of the cartridge module.

The fluid product distribution is therefore manually managed by the user who acts using a finger on the actuation member of the intermediate module. It is thus understood that the cartridge module is technically very simple, since it comprises no electric or electronic component and very few mechanical members. It constitutes an inexpensive replaceable cartridge or refill, that the user can easily separate and connect to the intermediate module, which is itself also relatively simple, since it mainly integrates mechanical transmission means, namely the means for transmitting vibrations and means for transmitting thrust, allowing to convert the movement of the actuation member thrust onto the reservoir. The motor module itself integrates the motor, its supply and its control, and constitutes, due to this, a complex and expensive module.

This separation of the applicator into three distinct modules, the first very simple, inexpensive and replaceable, the second also simple, but long-term and the third complex and expensive, allows to associate variouscartridge module models to a standard motor module by configuring the intermediate module such that it is adapted to the standard motor module and to the particular cartridge module. More specifically, the intermediate module is designed to transmit the vibrations from the motor module to the microneedles of the cartridge module and to distribute the fluid product contained in the reservoir(s) of the cartridge module. A suitable actuation member, and its possible suitable thrust transmission, are housed in the intermediate module.

The architecture of the microneedle applicator of the invention can thus be assimilated to a three-stage rocket, with an upper consumable stage, a lower technical stage and an intermediate vibration and actuation transmission stage.

Thus, a cosmetic product manufacturer can choose or design a particular cartridge module without being concerned about the motor module which will be associated with it, given that it is the intermediate module, particularly adapted both to the motor module and to the particular cartridge module, which will manage the transmission of vibrations and the actuation of the reservoir(s). The intermediate module thus allows to decorrelate the cartridge module of the motor module by playing a modular interface role. A broad choice of microneedle applicators can, due to this, be proposed for a reduced cost, since the motor module can be standard.

Advantageously, the intermediate module is also removably connected to the motor module, for example a screwed or bayonet connection. The removable connections allow a handling (connection and disconnection) without the intervention of an external utensil.

In a variant, the intermediate module can be definitively connected and fixed, or connected and fixed in a manner which is difficult to remove, to the motor module. In both cases, the two modules are initially separated, and in any case, integrated to one another inseparably.

Advantageously, the fluid product reservoir has a variable volume, the movement of the actuation member leading to a decrease in volume of the fluid product reservoir, such that at least some of its content is repelled upon each actuation to the fluid product outlet. Thus, the actuation member acts directly or indirectly on the reservoir without active intermediate member, like a pump or a motor. The cartridge module can comprise one single reservoir which is fully or preferably partially emptied upon each actuation. In a variant, the cartridge module can comprise several reservoirs which are successively emptied (partially or preferably fully) upon each actuation.

Advantageously, the fluid product reservoir can comprise a mobile or deformable wall, which is moved in response to the actuation of the actuation member about the longitudinal axis X or transversally to the longitudinal axis X.

According to a preferred design, the applicator can have a general pen configuration, adapted to be held between the thumb and the middle finger with the actuation member, which can be actuated by means of the index finger. It can also be held in the palm of the hand and actuated with the thumb.

According to another aspect of the invention, the cartridge module can be removably connected to the intermediate module by a connection combining an axial motion and a rotary motion, such as a screwing or a bayonet.

According to a first practical embodiment of the invention, the actuation member can comprise a lateral pushbutton which axially moves an actuation rod which acts progressively on the reservoir to repel successive doses of fluid product to the fluid product outlet. Thus, the transverse movement of the actuation member has the effect of axially moving the actuation rod which will bear on a mobile wall (deformable wall or scraper piston) of the reservoir. Each actuation generates a limited movement of the rod which will repel a fluid product dose of the reservoir, which can contain one or more doses, for example four. The rod fulfils a thrust transmission function: the transverse thrust on the actuation member is transformed into an axial thrust of the rod.

Advantageously, the actuation rod can be axially moved against a counter spring from a retracted starting position to several successive advanced positions, in which it is blocked in position against any backward elastic return by a catch device. Preferably, the catch device is provided with disengagement means to allow the catch device to release the actuation rod, which thus elastically returns to its retracted starting position. Advantageously, the disengagement means are constrained or blocked in an inoperative state by the connection of the cartridge module on the intermediate module and elastically released or not in a state disengaged by the separation of the cartridge module, the disengagement means advantageously comprising an engagement member which can be moved from a free state, corresponding to the disengaged state, to a constrained state, corresponding to the operative state, by a cam formed by the cartridge module and which can be moved from the constrained state to the free state by a counter spring, as soon as it is disengaged from the cam.

Thus, in this single reservoir embodiment, the connection of the cartridge module to the intermediate module has the effect of neutralising the disengagement means, which remain inoperative until the cartridge module is removed from the intermediate module. The disengagement means, associated with the removal of the cartridge module, fulfil a reset function for the actuation rod, whatever its advanced position, which thus automatically returns into its retracted starting position: the user does not need to carry out any handling to bring the rod back into the starting position.

The engagement between the cam of the cartridge module and the engagement member of the disengagement means also fulfils an authenticity module of the cartridge module, as this engagement is comparable to that which exists between a lock and a key. More generally, it can thus be said that the cartridge module and the intermediate module together form specific identification means which guarantee the authenticity of the cartridge module. These specific identification means can be constituted by the engagement between the cam of the cartridge module and the engagement member of the disengagement means, but can also be constituted by any cooperative or complementary engagement between these two modules.

Of course, in the absence of any engagement member and cam, it is down to the user to actuate the disengagement means to reset the rod.

It must be noted that the axially moving actuation rod, associated with a catch device and advantageously with disengagement means is a characteristic which can be implemented in an applicator only comprising two modules, namely a motor module integrating the motor, the actuation member, the rod, the catch device and advantageously disengagement means, and a cartridge module, identical or similar to that already described, which can serve to neutralise/release the disengagement means during its assembly/removal. In other words, a protection could be sought for these characteristics in a two-module applicator, and even an applicator with one single module, with the replaceable reservoir.

According to a second practical embodiment of the invention, the cartridge module can comprise a rotary cylinder supporting several fluid product reservoirs, which can thus in turn be brought back into an emptying position, the intermediate module comprises a lateral pushbutton which acts on the reservoir located in the emptying position to repel its content to the fluid product outlet.

According to a first variant, the lateral pushbutton can axially move an actuation rod against a counter spring from a starting position to an extended position corresponding to the maximum emptying of the reservoir. The actuation rod fulfils a thrust transmission function: the transverse thrust on the pushbutton is transformed into an axial thrust of the rod.

According to a second variant, the lateral pushbutton can act directly on the reservoir through a lateral window of the cylinder. Advantageously, the intermediate module can comprise actuation means to rotate the cylinder of the cartridge module. Preferably, the application face of the cartridge module can be blocked in rotation by the intermediate module, each reservoir comprising a removable blocking member which is removed before it arrives in the emptying position by an opening member integral with the application face. The reservoirs can, for example, be presented in the form of small, flexible vials with a blocking head which is cut by a fixed blade just before returning to the emptying position, in which the pushbutton will flatten it and repel its content to the outlet at the level of the application face.

It must be noted that the rotary cylinder with several reservoirs with lateral or axial actuation is a characteristic which can be implemented in an applicator only comprising two modules, namely a motor module integrating the motor and the lateral pushbutton, and a cartridge module with a cylinder, identical or similar to that already described. In other words, a protection could be sought for these characteristics in a two-module applicator, and even an applicator with one single module, with replaceable reservoirs.

According to another aspect, the application face can comprise a plate equipped with microneedles and passed through by the fluid product outlet. The fluid product outlet can also be made at the periphery of the application face.

Advantageously, the applicator can further comprise means for adjusting the penetration depth of the microneedles, acting advantageously on the axial position of the motor in the first module. Indeed, it is sometimes useful to make the microneedles penetrate more or less, according to the cosmetic product, to the desired treatment or the quality and the nature of the skin.

The applicator can also comprise means for controlling the motor, which deactivate it automatically when the modules are not connected. This is for safe use.

The scope of the invention resides in the action of segmenting the three-module microneedle applicator device, units or subunits, with a standard module, a bespoke disposable module and a median module which makes the transmission between the two other modules and which integrates the means for repelling the fluid product outside of the reservoir(s) to the application face of the disposable module, which comprises microneedles. The invention will now be fully described in reference to the appended drawings which give, as non-limiting examples, several embodiments of the invention.

Figure 2:
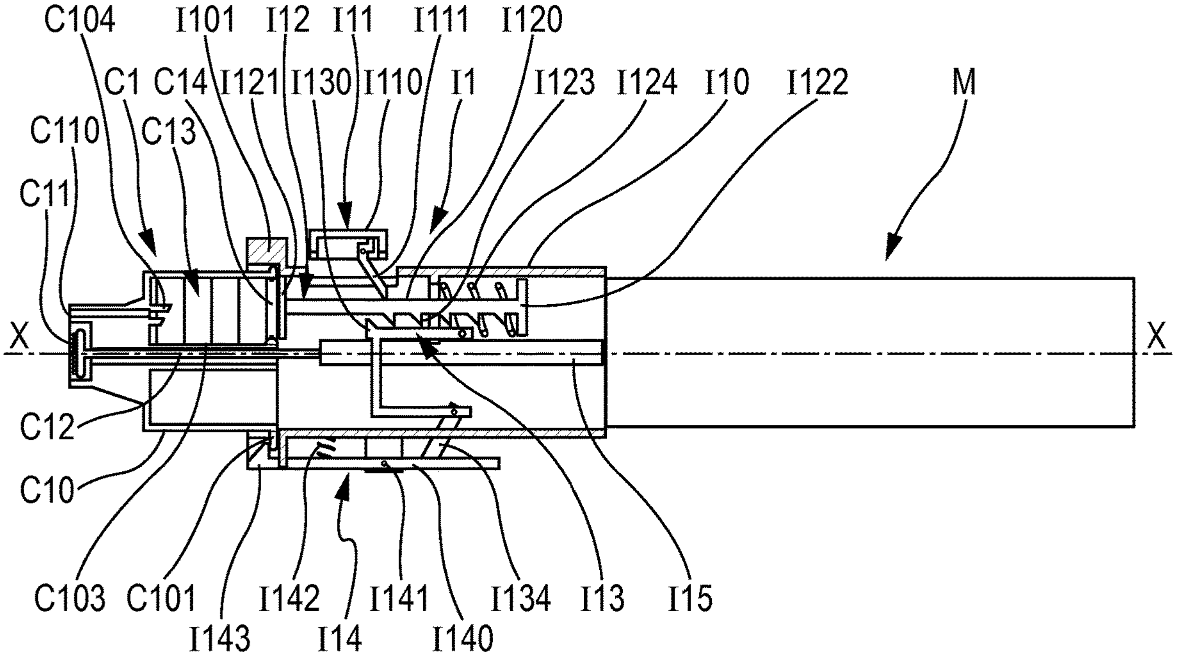
Figure 3:
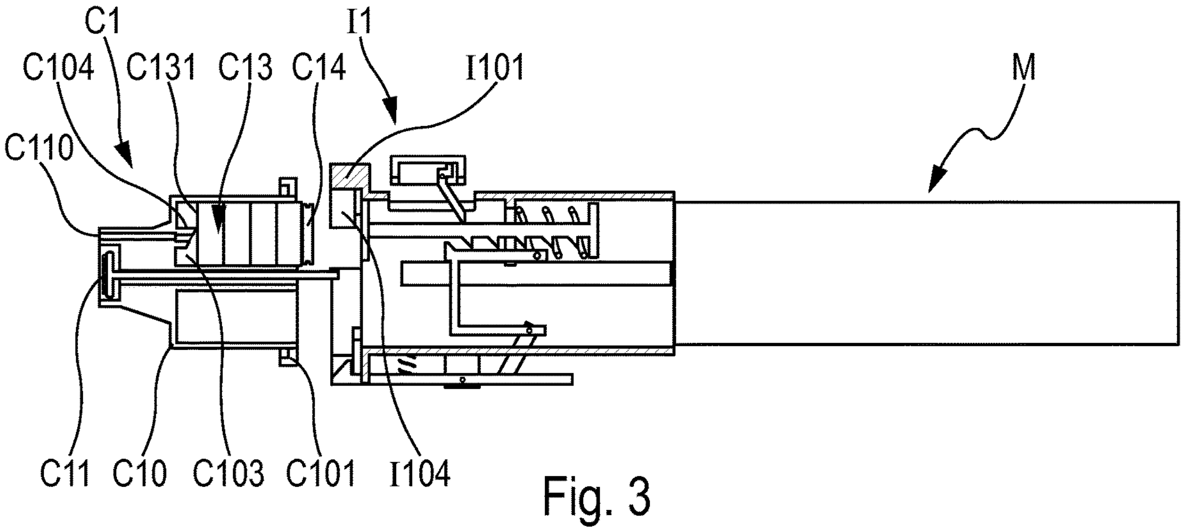
Figure 4:
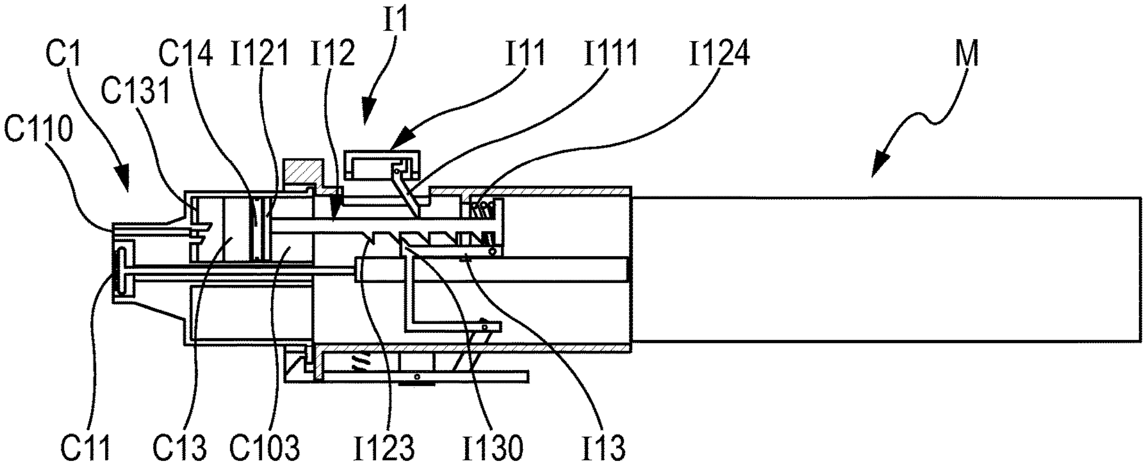
Figure 5:
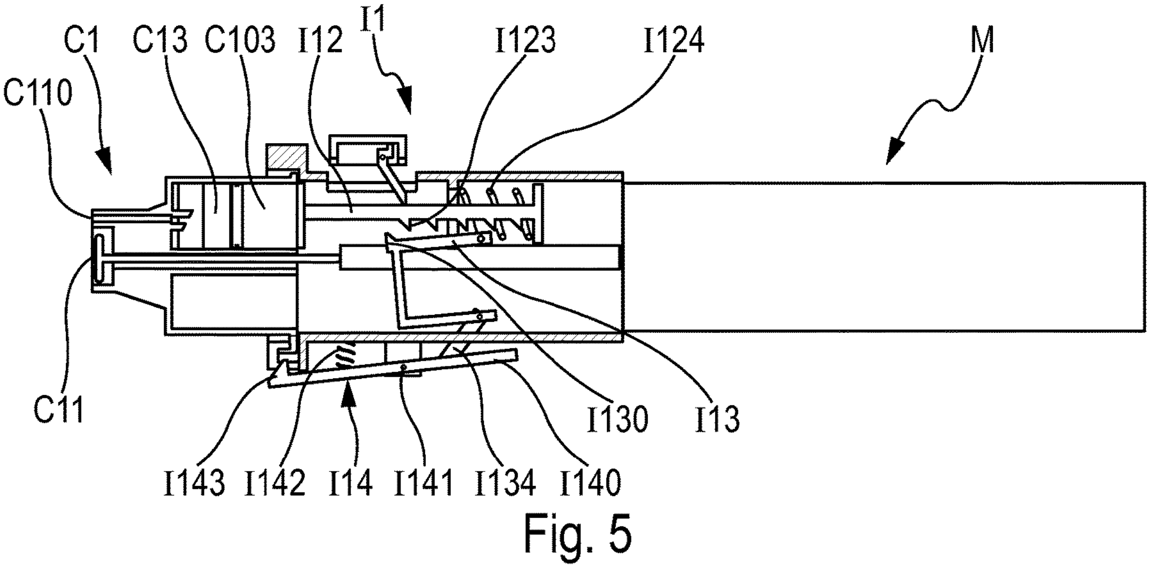
Figure 6A:
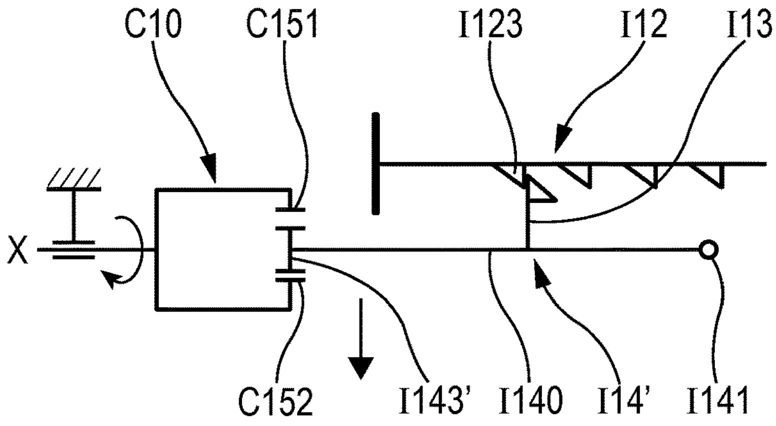
Figure 6B:
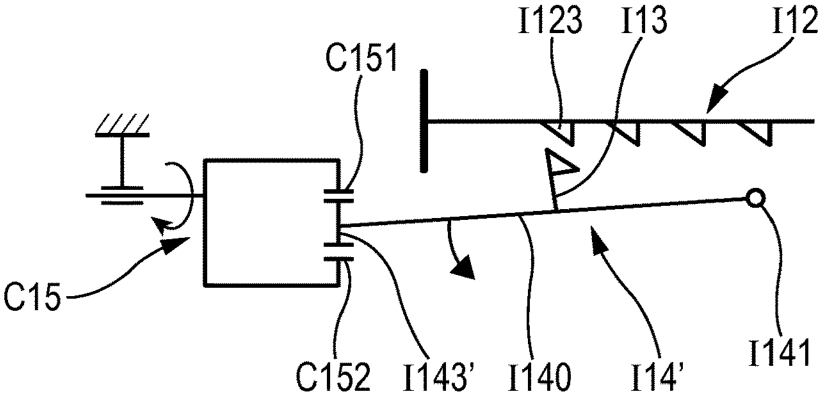
Figure 7A:
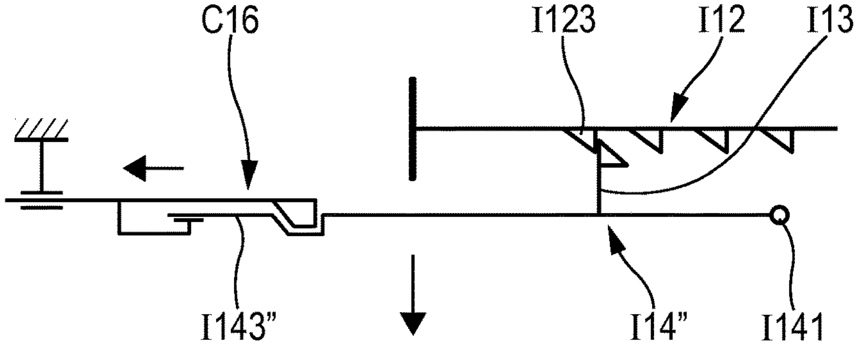
Figure 7B:
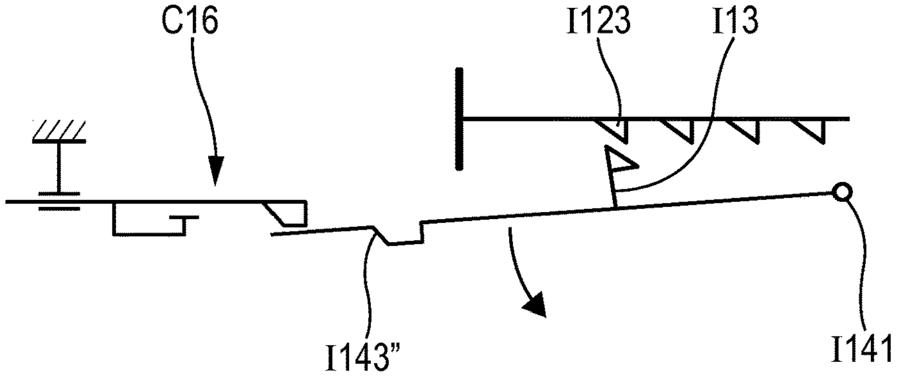
Figure 8:
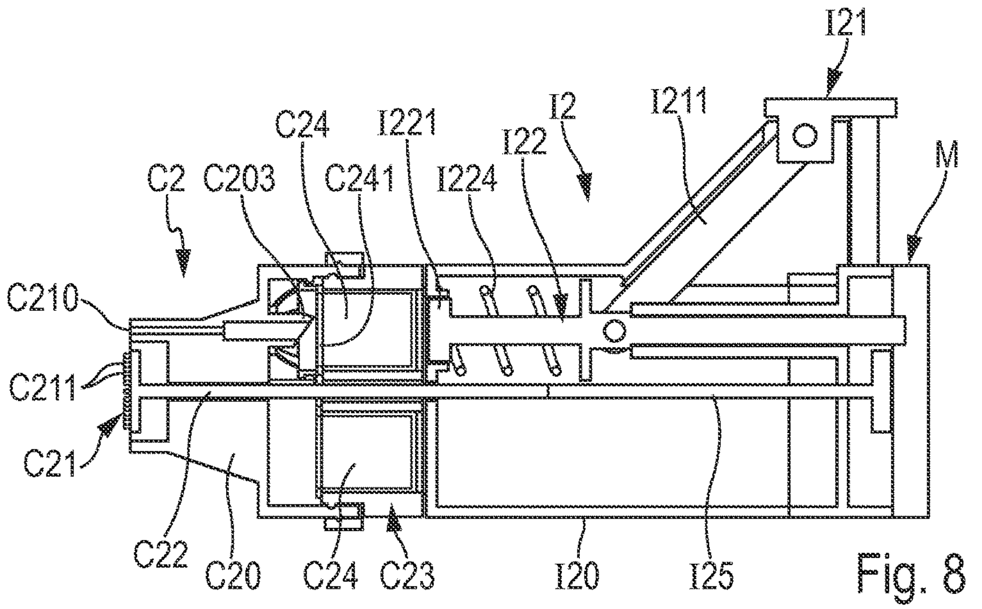
Figure 9A:
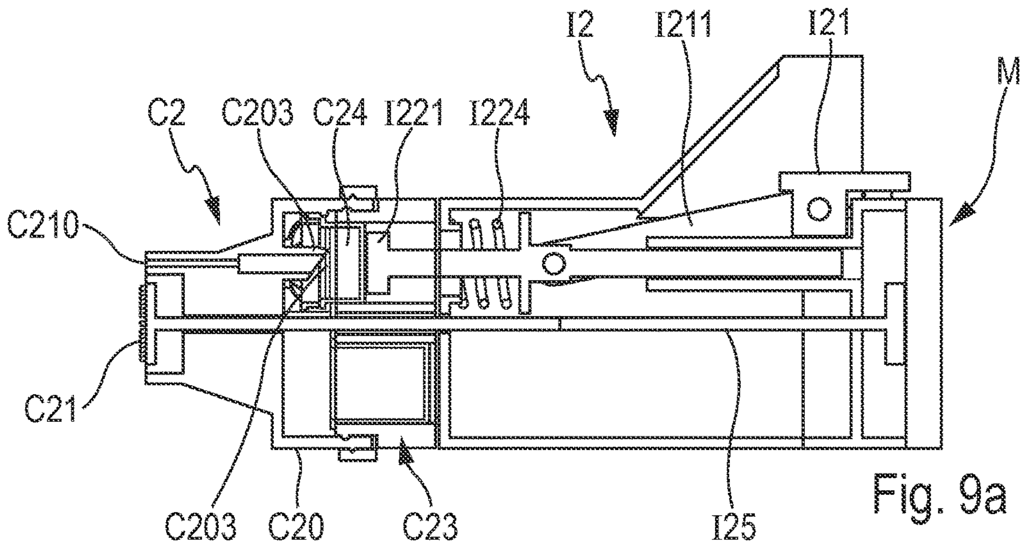
Figure 9B:
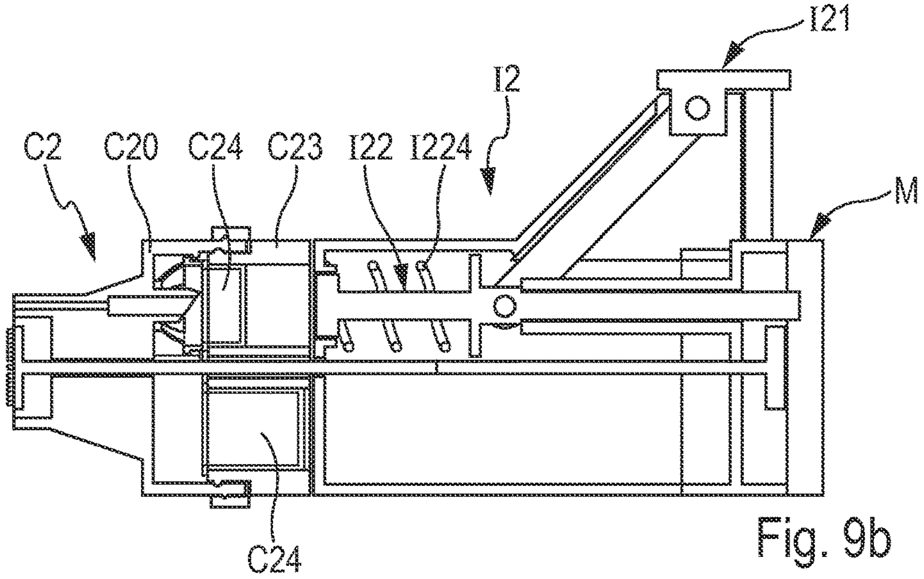
Figure 10A:
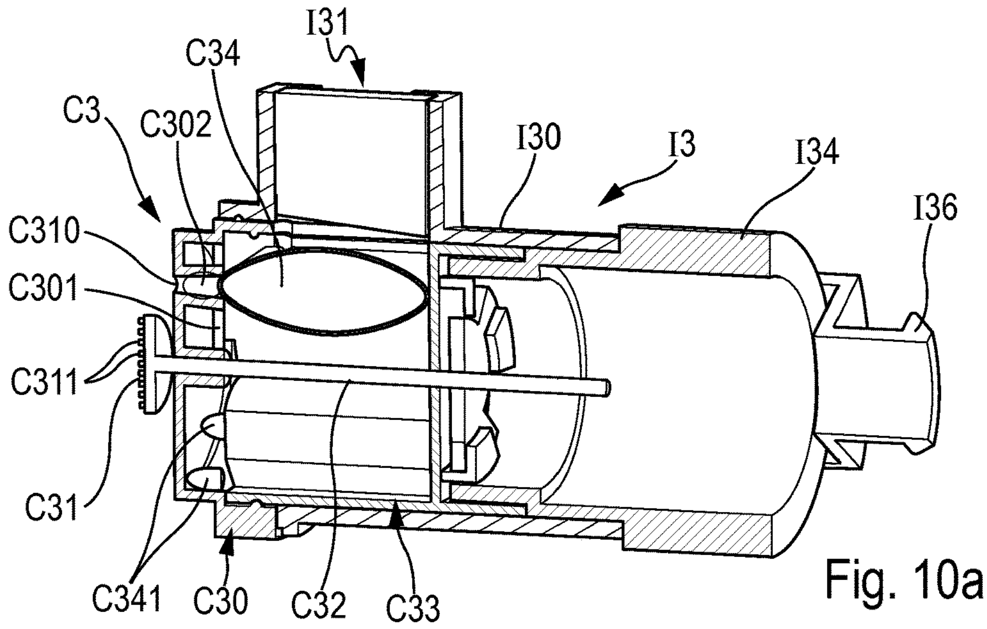
Figure 10B:
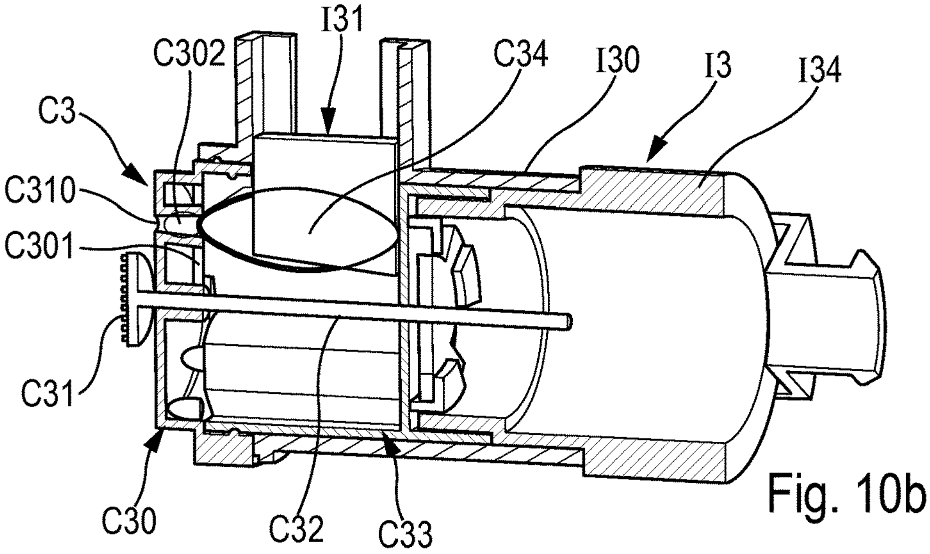
Figure 11:
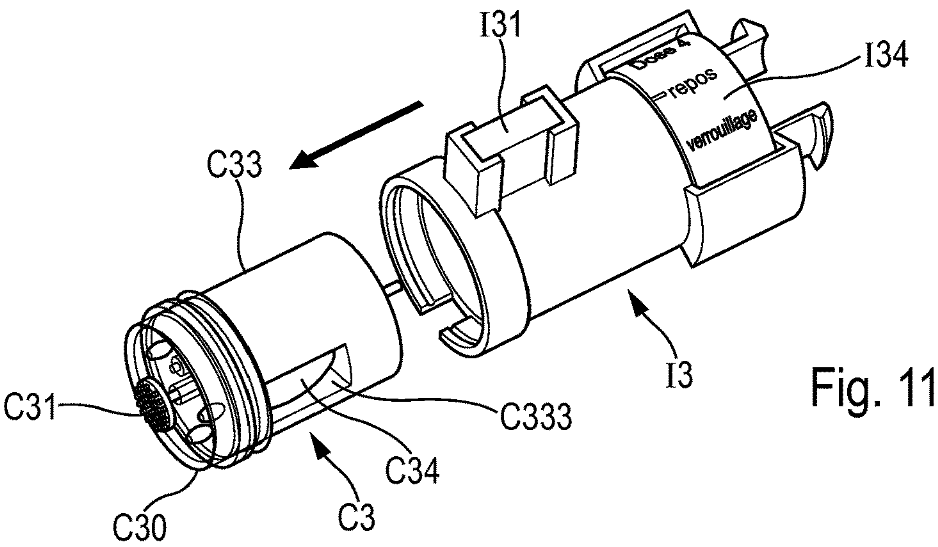

In the figures:

FIG. 1 is a schematic, perspective, locally cross-sectional view of a microneedle applicator according to a first embodiment of the invention, FIG. 2 is a transverse, vertical, axial, cross-sectional view through the applicator of FIG. 1, FIG. 3 is a view similar to that of FIG. 2 with the applicator in a disassembled state, FIG. 4 is a similar view of FIGS. 2 and 3 with the already-actuated applicator, FIG. 5 is a view similar to those of FIGS. 2 to 4 with the applicator in a disengaged state, FIGS. 6*a* and 6*b* are very schematic representations aiming to illustrate an embodiment of the disengagement means and their actuation, FIGS. 7*a* and 7*b* represent another embodiment for the disengagement means and their actuation, FIG. 8 is a vertical, transverse, cross-sectional view through the cartridge and intermediate modules of an applicator according to a second embodiment of the invention, FIGS. 9*a* and 9*b* are views similar to that of FIG. 8, respectively in actuated and return positions, FIGS. 10*a* and 10*b* are vertical, transverse, cross-sectional views through an applicator of the invention according to a third embodiment, respectively in the rest state and in the actuated state, and FIG. 11 is a perspective view of the applicator of FIGS. 10*a* and 10*b* in the disassembled state.

The applicator of the invention is purely cosmetic, even dermatological, excluding tattooing. It associates two treatment means, namely the distribution of a cosmetic product, which can be a cream, a balm, a lotion, a serum, etc., and the perforation of the stratum corneum to reach the epidermis, without touching the dermis, by means of microneedles. According to the nature of the cosmetic product and the result sought, the cosmetic product is applied before, at the same time or after the micro-perforation. The applicator of the invention is rather for domestic use, in that the user of the applicator will use it on itself. It can, however, be used professionally.

In the three embodiments of the invention illustrated in the figures, the applicator of the invention comprises three distinct modules, namely a first motor module M, a second cartridge module C1, C2, C3 and a third intermediate module I1, I2, I3, assembled or interposed between the motor M and cartridge C1, C2, C3 modules: the intermediate module I1, I2, I3 thus joins between the motor M and cartridge C1, C2, C3 modules. The three modules are disposed about a longitudinal axis X. The intermediate module I1, I2, I3 is connected, advantageously removably, to the motor module M. A definitive connection between these two modules can be considered. The intermediate module I1, I2, I3 is connected, advantageously removably, to the cartridge module C1, C2, C3. A definitive connection can be considered in certain cases. Preferably, the modules can be connected and disconnected simply and rapidly, by the user themselves, for example using both their hands by impressing a torque and/or a thrust/traction between two modules. When the three modules are assembled, the applicator has a general, pen-shaped configuration about the longitudinal axis X. The applicator can moreover be held in the same way as a pen.

The first motor module M can be common to the two embodiments. It will not be described in detail, as it is not critical for the invention. It can be a standard, commercial module. In FIG. 1, it can be seen that the motor module M contains a motor M1, which is preferably an electric motor. It can be a small rotary motor which rotates a shaft M10 on itself. An electromagnet motor can also be provided, a linear or a piezoelectric motor. The motor M1 is powered by a battery M2 and controlled by electronics M3, which will manage the rotation speed of the shaft M10, the activation sequences and durations of the motor, etc. An external activation button M21 allows the user to switch the applicator on. The free end of the shaft M10 is capped by a casing M5, allowing to transform the rotation of the shaft M10 in a vibratory axial oscillation transmitted by an output shaft M50, intended to be connected to the intermediate module.

Of course, this is only one non-limiting embodiment: any motor module M adapted to generate an axial vibration can be implemented in the scope of the present invention, given that the motor module M is not critical for the invention.

Now, FIG. 2 will be referred to, to describe in detail, the structure of the cartridge module C1 and of the intermediate module I1 of an applicator according to a first embodiment of the invention.

The cartridge module C1 comprises a cartridge body C10 which comprises at one of its ends, a connecting collar C101 and at its other end, a fluid product outlet orifice C110. The cartridge module C1 comprises an application face C11 which is provided with several microneedles C111. This application face C11 is disposed adjacently to the fluid product outlet C110. The application face C11 is connected to a vibrating transmission rod C12 which passes through the cartridge body C10. The cartridge C1 also contains a fluid product reservoir C13 which is slidingly disposed in a chamber C103 formed by the cartridge body C10. At the bottom of this chamber C103, the cartridge body C10 forms a perforating needle C104 which communicates directly by a conduit to the fluid product outlet orifice C110. The fluid product reservoir C13 comprises a pusher piston C14 which is slidingly assembled inside the reservoir so as to vary its useful volume. The fluid product reservoir C13 can thus be presented in the form of a cylinder provided with one of its ends of the pusher piston C14 and at its other end of a pierceable membrane C131 intended to be pierced by the piercing needle C103 of the cartridge body C10. The fluid product reservoir C13 can moreover be a component which can be removed from the body C10 after use and replaced by a new replacement reservoir.

The cartridge module C1 is removably connected, in particular by rotation (bayonet or screwing), to the intermediate module I1 which comprises, to this end, a connecting crown I101 in which the collar C101 can be received stably after rotation. This connecting crown I101 is formed by a body I10 which is also connected, advantageously removably, to the motor module M. The connection can be made by screwing, bayonet or snap-fitting. A definitive connection is also possible. The intermediate module I1 comprises an actuation member I11 which can be presented in the form of a lateral pushbutton, which is therefore moved perpendicularly to the axis X. This actuation member I11 can project with respect to the body I1 through a lateral window of the body I10. The actuation member I11 comprises thrust pads I111, the function of which will be given below. These pads I111 extend in an inclined manner to the inside of the body I10. The intermediate module I1 also comprises an actuation rod I12 which extends parallel to the axis X. This rod I12 comprises a thrust plate I121 intended to come into contact with the pusher piston C14 of the reservoir C13 of the cartridge module C1. The rod I12 comprises, on its length, several teeth I123, as well as thrust pins (not represented). The end opposite the thrust plate I12 forms a stub 1122 on which bears a counter spring I124. Thus, the actuation rod I12 is urged in extension from the pusher piston C14 by the counter spring I124. The movement of the actuation rod I12 in the direction of the pusher piston C14 is generated by the sinking of the actuation member I11, of which the thrust pads I111 engage with the thrust lugs (not represented) of the actuation rod I12. The inclined orientation of the thrust pads I111 has the effect of moving the actuation rod I12 in the direction of the pusher piston C14.

The intermediate module 10 also comprises a catch device I13 which comprises a catch I130 intended to successively engage with the teeth I123 of the actuation rod I12. In other words, the catch device I13 allows the actuation rod I12 to maintain its position after each actuation of the actuation member I11. Without this catch device I13, the rod I12 would, each time, return into its original position, urged by the counter spring I124. The catch device I13 thus allows to neutralise the urging of the spring I124.

The intermediate module I1 also comprises disengagement means I14 which allow to disengage the catch device I13 of the actuation rod I12. These disengagement means I14 can, for example, comprise a plate I40 which is mounted pivoting on an axis I141 integral with the body I10. This plate I40 is also connected to the catch device by a connecting rod I134. At its end, the plate I140 comprises an engagement member I143 which engages with the crown I101. Finally, a spring I142 urges the plate I140 so as to disengage the engagement member I43 from the crown I101, the functioning of these disengagement means will be explained below.

The intermediate module I1 also comprises a bar for transmitting vibrations I15 which connects the shaft M50 of the motor module M to the transmission rod C12 of the cartridge module C1.

In FIG. 3, the applicator is seen with the cartridge module C1 disconnected from the intermediate module I1. The connecting collar C11 is disengaged from the connecting crown I101. It can thus be noted that the reservoir C13 is not completely engaged inside the chamber C103 of the body C10: the piercing needle 104 has not yet penetrated the membrane C131 of the reservoir C13 such that the pusher piston C14 projects outside of the body C10. The cartridge module is in its initial position before use, in which the reservoir C13 is hermetically blocked. During the connection of the cartridge module C1 on the intermediate module I1, a thrust pad 1104 formed by the body I10 will push the reservoir C13 in the direction of the piercing needle 104 so as to perforate the membrane C131 of the reservoir C13, which is thus located in its position of use. Subsequently, all the user needs to do, is to impress a rotational motion to the cartridge module C1 to engage its collar C101 in the connecting crown I101 of the intermediate module I1. Once connected, the thrust plate I121 of the actuation rod I12 comes into contact, slightly pressed or not against the pusher piston C14 of the reservoir C13. The intermediate module I1 is in its starting configuration, also represented in FIG. 2.

The user can thus exert a thrust on the actuation member I11 so as to sink it into the body I10 of the intermediate module I1. In doing this, the thrust pads I111 will engage with the thrust lugs (not represented) of the actuation rod I12 which is thus axially moved against the pusher piston C14. At the end of actuation, a tooth I123 of the rod I12 will engage with the notch I130 of the catch device I13. After two successive actuations, the applicator is found in the configuration represented in FIG. 4. Two fluid product doses have been distributed through the fluid product outlet C110 located in the proximity of the application face C11 equipped with microneedles C111. It can be noted in FIG. 4, that two fluid product doses still remain to be distributed. After each dose is distributed, a tooth I123 of the rod I12 will engage with the notch I130 of the catch device I13.

Thanks to the disengagement means I14, the user can, at any time, return the actuation rod I12 into its initial position. This is represented in FIG. 5. It can be seen there, that the plate I140 is pivoted about its axis I141 so as to disengage its engagement member I143 of the crown I101. This disengagement is moreover favoured by the spring I142. To reach this position, all the user needs to do, is to press on the plate I140 to the right of the pivoting axis I141. The plate I140 will thus move the connecting rod I134 which will make the catch device I13 tilt so as to disengage its notch I130 of the tooth I23 from the rod C12 with which it was engaged. It can be seen in FIG. 5, that the notch I130 is extended from the first tooth I123 and that the rod I12 has returned to its initial position under the action of the counter spring I124.

In this embodiment, the intermediate module I1 therefore allows to act successively on a fluid product reservoir C13 to deliver successive fluid product doses. The catch device I13 allows to maintain the position of the rod I12 after each actuation and the disengagement means I14 allow to return the rod I12 into its initial position. The actuation of disengagement means is here manual, in that the user must act on the plate I40 to disengage the catch device I13 from the actuation rod I12.

By referring to FIGS. 6*a* and 6*b*, it can be seen very schematically how the actuation of the disengagement means can be automatic. The thrust rod I12 is schematically represented with its thrust plate and its teeth I123. The catch device I13 is also represented very schematically. The disengagement means I14' also comprise a plate or a rail I140 mounted pivoting about an axis I141. At its other end, the disengagement means I14' comprise an engagement member I143' which is engaged between two cams C151 and C152 formed by the body C10 of the cartridge module C1. The cams C151 and C152 are inclined or off-centre, so as to be able to move the engagement member I143' about the pivoting axis I141. FIG. 6*a* represents the disengagement means I14' in an operative state, with the catch device I13 engaged with a tooth I123 of the actuation rod I12. This operative position is reached when the cartridge module C1 is connected to the intermediate module I1.

In FIG. 6*b*, it can be seen that the cam C151 has driven the plate or rail I140 downwards by pivoting about the pivoting axis I141. The catch device I13 is thus disengaged from the tooth I123 of the rod I12. This disengaged configuration is reached when the cartridge module C1 has been rotated with respect to the intermediate module I1 until it can be disconnected. The plate or rail I140 can be maintained in the disengaged position of FIG. 6*b* by a spring, comparable to the spring I142 of the preceding figures.

Through this very schematic embodiment, it can be understood that the disengagement means I14' can be actuated automatically, simply by the connection/disconnection of the cartridge module C1 on the intermediate module I1, using a rotation of the cartridge module C1 with respect to the intermediate module I1. Thus, the user does not even need to be concerned about returning the actuation rod I12 to its initial position, since the separation of the cartridge module C1 from the intermediate module I1 automatically leads to the actuation of the disengagement means which allow to bring the rod I12 back into its retracted rest position.

FIGS. 7*a* and 7*b* are extremely schematic views aiming to make it understood that the actuation of the disengagement means can also be obtained by a purely axial movement of the cartridge module C1 with respect to the intermediate module I2. The disengagement means I14" comprise an engagement member I143" engaged with a housing C16 formed by the cartridge module C1, when the cartridge module C1 is connected to the intermediate module I1. The catch device I13 is thus engaged with a tooth I123 of the actuation rod I12.

As soon as the cartridge module C1 is disconnected from the intermediate module I1, the engagement member I143" is disengaged from the housing C13 and the disengagement means can thus pivot about the axis I141, so as to disengage the catch device I13 of the tooth I123. This is represented in FIG. 7*b*.

This schematic example aims to make it understood that the actuation of the disengagement means can also be achieved by a translative movement of the cartridge module C1 with respect to the intermediate module I1.

This intermediate module I1, with its lateral actuation member I11, its actuation rod I12 with axial movement, its catch device I13 and its manual I14 or automatic I14' or I14" disengagement means, is preferably removably connected both to the motor module M and to the cartridge module C1. However, embodiments in which this intermediate module I1 can be integrated to the motor module M and/or to the cartridge module C1 can be imagined. A one-piece applicator with the possibility of replacing the reservoir C13 through an access window can even be imagined. Particularly, the disengagement means constitute a characteristic which can be implemented in any applicator comprising a multiple-dose reservoir.

The next two embodiments which are going to be described have several characteristics in common. First, the intermediate module comprises a thrust member which acts on the reservoir of the cartridge module so as to return each time into its initial starting position. Therefore, there is no successive advancement, like in the first embodiment of the invention. As regards the cartridge module, it integrates a rotary cylinder filled with several reservoirs: the user can make the cylinder rotate to bring a reservoir back to the right of the thrust member such that the reservoir can be majorly or preferably totally emptied. Then, all the user needs to do is make the rotary cylinder rotate to bring the next reservoir to the right of the thrust member. It will be seen that the rotation of the rotary cylinder can be achieved directly at the level of the cartridge module or also at the level of the intermediate module. Of course, the intermediate module comprises vibration transmission means allowing to transmit the vibrations generated by the motor module M to the application face provided with microneedles of the cartridge module. Also, the motor module M can be removably connected to the intermediate module, just like in the first embodiment of the invention. Likewise, the intermediate module can be removably connected by a rotation motion or a simple axial translation motion to the cartridge module.

Now, FIGS. 8, 9*a* and 9*b* will be referred to, to describe the second embodiment of the invention. The motor module M, which is only very schematically represented, can be identical or similar to that of the first embodiment. The intermediate module I2 comprises a body 120 which is passed through by a vibration transmission member I25 which extends substantially or completely axially. The body 120 contains an actuation rod I22 which axially moves. This actuation rod I22 is urged by a spring I224 in the direction of the motor module M. The rod I22 comprises a thrust plate I221 intended to come into contact with one of the reservoirs of the cartridge module, as will be seen below. The rod I22 is connected to an actuation member I21 by a connecting rod I211. The actuation member I21, like in the first embodiment, can be moved perpendicularly to the axis of the applicator. The connecting rod I211 serves to transform the transverse or lateral movement of the actuation member I21 into a purely axial movement of the actuation rod I22. The sinking of the actuation member I21 into the body 120 is done against the force exerted by the counter spring I224 which allows to bring the rod I22 back, as well as the actuation member I21 into its extended starting position, such as represented in FIGS. 8 and 9*b*. In its completely sunken position, the actuation member I21 is located in the configuration represented in FIG. 9*b*. Thus, upon each thrust on the actuation member I21, the actuation rod I22 is moved from an initial starting position (FIG. 8 or 9*b*) in a maximum extended position (FIG. 9*a*), then returns under the action of the counter spring I224 into its initial starting position. Therefore, there is no intermediate position, like in the first embodiment of the invention. The mechanism of the intermediate module I2 is therefore simpler than that of the intermediate module I1 of the first embodiment.

The cartridge module C2 comprises a body C20 which is fixed with respect to the body I1 of the intermediate module I2 once the cartridge module C2 is in place on the intermediate module I2. This cartridge module C2 supports the application face C21 provided with microneedles C211. The application face C21 is connected to a rod or rail for transmitting vibrations C22 intended to be coupled to the vibration transmission member I25 of the intermediate module I2. The body C20 also defines a fluid product outlet C210 which is located in the proximity of the application face C21. This fluid product outlet C210 is connected by a conduit inside a piercing needle C203. The cartridge module C2 also comprises a rotary cylinder C23 which is mounted rotary on or in the body C20. This cylinder C23 can be rotated by the user at the level of its accessible outer periphery. The cylinder C23 contains several reservoirs C24, which can be presented in the form offlattenable pockets or piston reservoirs. Each reservoir C24 comprises a pierceable front wall 241 intended to be pierced by the piercing needle C203. In the initial position, the membrane C241 is intact and disposed adjacently to the piercing needle C203, like can be seen in FIG. 8. In this initial starting position, the thrust plate I221 of the actuation rod I22 is disposed in the proximity of the bottom of the reservoir C24. A lateral thrust on the actuation member I21 has the effect of moving it, which leads to, by way of the connecting rod I211, the axial movement of the actuation rod I22, of which the member in the thrust plate I221 will first move the reservoir C23 in its cylinder to pierce the membrane 241, then to flatten the reservoir so as to repel its content to the level of the fluid product outlet 210. FIG. 9*a* represents the completely sunken position with the thrust plate I221 having reached its maximum advanced position. The reservoir C24 is empty or practically empty.

As soon as the user relaxes its pressure on the actuation member I21, this returns into its initial starting position under the action of the force of the counter spring I224. Thus, this is found in the configuration represented in FIG. 9*b*. Thus, all the user needs to do, is to make the cylinder C23 rotate to bring another reservoir C24 to the face of the thrust plate I221 of the actuation rod I22. A complete cycle is thus achieved.

In this embodiment, the cartridge module C2 in its entirety can be replaced once all its reservoirs C24 have been emptied. In a variant, it is also possible that only the cylinder C23 is replaced or also that only the reservoirs C24 are replaced by preserving the cylinder C23. It is thus seen that several formulas are possibly by preserving the same architecture for the cartridge module C2.

It can also be considered to implement the cartridge module C2 on a main module integrating both the motor module M and the intermediate module I2. In other words, the actuation means of the intermediate module I2 would be integrated to a common or main module integrating all the means to actuate both the application face C21 and the reservoirs C24.

FIGS. 10*a*, 10*b* and 11 represent the third embodiment of the invention, in which the cartridge module C3 also integrates a rotary cylinder C33 receiving several reservoirs C34. Just like in the second embodiment, all of the cartridge module C3 can be replaced, or only its cylinder C33 or also only its reservoirs C34. The cartridge module C3 comprises a fixed body C30 which forms the fluid product outlet C310, as well as a cutting blade C301, the function of which will be given below. The application face C31, with its microneedles C311, is positioned in the direct proximity of the fluid product outlet C310. This application face C31 is extended by a rod or by a rail for transmitting vibrations C35 intended toengage with the vibration transmission means (not represented) of the intermediate module 13. The rotary cylinder C33 is received in a rotary manner on or in the body C30. The rotary cylinder C33 comprises lateral windows C333 giving access to the reservoirs C34, which comprise a removable blocking member C341 which projects into a conduit C302 leading to the level of the fluid product outlet C310. Thus, when the cylinder C33 is rotated, its blocking member C341 engages with the cutting blade C301 which separates it from the remainder of the reservoir. In FIG. 10*a*, a removable blocking member can be seen 341 fallen to the bottom of the body C30. This blocking member C341 is that of the reservoir C34 disposed opposite the conduit C302. It is also understood that the reservoir disposed below C34 also has its removable blocking member C341 pointing into the body C30. It can thus be said that the cutting blade C301 acts as a member for opening the reservoir C34 by rotation of the cylinder C33. Advantageously, the reservoirs C34 can be presented in the form of small vials which can be flattened, made of deformable material.

The intermediate module I3 comprises a body 130, in which a rotary actuation ring 134 is received, which engages with the cylinder C33, so as to be able to rotate it. It is seen in FIG. 11 that the actuation ring 134 comprises indications of use which can be seen through a window of the body 130.

The intermediate module I3 also comprises an actuation member I31, which is presented very simply by a lateral pushbutton that the user can sink using a finger. This lateral pushbutton can have the form of a pad, the guiding of which is ensured by a funnel formed by the body 130. When a reservoir C34 is positioned below the actuation member I31, its removable blocking member C341 has already been removed by the blade C301. This configuration is represented in FIG. 10*a*. Thus, all the user needs to do is press the actuation member I31 to engage with the flexible reservoir C34, so as to flatten it. This configuration is represented in FIG. 10*b*. The fluid product of the reservoir C34 is thus repelled through the conduit C302 to the level of the fluid product outlet C310. When the user relaxes their push on the actuation member I31, it returns into its rest position, either by a counter spring not represented, or by the elastic memory of the reservoir C34 which returns to its initial position after emptying. After application of the fluid product using the application face 31 on the skin of the user, the latter can make the actuation ring 134 rotate to bring the next reservoir below the actuation member I31 and to repeat the operation.

It can be noted that in this embodiment, the cartridge module C3 is practically fully received inside the intermediate module I3, only its body C30 projecting frontwards.

Although not represented, it can be imagined that the intermediate module I3 comprises an access hatch allowing to access the lateral windows C333 of the cylinder to remove and insert reservoirs C34.

The intermediate module I3 comprises connecting means I36 adapted to engage with the motor module M.

In the three embodiments which have just been described, the microneedle applicator of the invention comprises three distinct modules or stages which are connected to one another, preferably removably. The intermediate module I1, I2, I3 always comprises an actuation member I11, I21, I31 and vibration transmission means I15, I25. The cartridge module C1, C2, C3 always comprises an application face C11, C21, C31 equipped with microneedles C111, C211, C311, as well as a fluid product outlet C110, C210, C310. It also comprises a vibration transmission member allowing to connect the application face to the vibration transmission means of the intermediate module.

Although certain characteristics have been described in relation to this three-stage architecture in the module, it must be understood that these characteristics could be implemented in different architectures. In particular, the actuation means of the first embodiment could be integrated in any microneedle applicator, whether it is constituted of one, two or three stages or modules. Likewise, the rotary cylinder C23, C33 has been described in relation to this three-stage or three-module architecture. However, these cylinders could also be implemented in any microneedle applicator, whether it comprises three stages, two stages or only one stage.

The three-stage architecture in the module of the invention mainly aims to be able to adapt a great variety of cartridge modules to a standard motor module, thanks to the adaptability and to the modularity of the intermediate stage.

The invention claimed is:

1. A microneedle applicator for applying a fluid product on the skin and for making it penetrate into the skin, the applicator defining a longitudinal axis X and comprising:

an application face provided with at least one fluid product outlet and with several microneedles, a motor for making the microneedles vibrate, a fluid product reservoir connected to the fluid product outlet, an actuation member for conveying the fluid product from the fluid product reservoir to the fluid product outlet, three distinct modules axially connected to one another, namely:

a motor module housing the motor and accessories for making the motor function, a cartridge module housing said fluid product reservoir and forming the application face, an intermediate module connected to the motor module and removably connected to the cartridge module, the intermediate module comprising the actuation member and transmission means for transmitting the vibrations generated by the motor of the motor module to the microneedles of the cartridge module.

2. The applicator according to claim 1, wherein the intermediate module is removably connected to the motor module.

3. The applicator according to claim 1, wherein the fluid product reservoir has a variable volume, the movement of the actuation member leading to a decrease in volume of the fluid product reservoir, such that at least some content of the fluid product reservoir is repelled to the fluid product outlet.

4. The applicator according to claim 1, wherein the fluid product reservoir comprises a mobile or deformable wall, which is moved in response to the actuation of the actuation member about the longitudinal axis X or transversally to the longitudinal axis X.

5. The applicator according to claim 1, having a general pen configuration, adapted to being held between the thumb and the middle finger with the actuation member which can be actuated by means of the index finger.

6. The applicator according to claim 1, wherein the cartridge module is removably connected to the intermediate module by a connection combining an axial motion and a rotary motion, such as a screwing or a bayonet.

7. The applicator according to claim 1, wherein the actuation member comprises a lateral pushbutton which axially moves an actuation rod which acts progressively on the fluid product reservoir to repel successive fluid product doses to the fluid product outlet.

8. The applicator according to claim 7, wherein the actuation rod can be axially moved against a counter spring from a retracted starting position to several successive advanced position, in which the actuation rod is blocked in position against any backward return by a catch device.

9. The applicator according to claim 8, wherein the catch device is provided with disengagement means to allow the catch device to release the actuation rod, which thus elastically returns to the retracted starting position.

10. The applicator according to claim 9, wherein the disengagement means are constrained in an inoperative state by a connector of the cartridge module on the intermediate module and elastically released in a disengaged state by the separation of the cartridge module, the disengagement means comprising a catch configured to be moved from a free state, corresponding to the disengaged state, to a constrained state, corresponding to an operative state, by a cam formed by the cartridge module and to be moved from the constrained state to the free state by a counter spring when disengaged from the cam.

11. The applicator according to claim 1, wherein the cartridge module comprises a rotary cylinder supporting several fluid product reservoirs, which can thus be brought, in turn, into an emptying position so that the actuation member acts on a fluid product reservoir, from the several fluid product reservoirs, located in the emptying position to repel content of the fluid product reservoir located in the emptying position to the fluid product outlet.

12. The applicator according to claim 11, wherein the actuation member comprises an axially moveable actuation rod configured to move against a counter spring from a starting position to an extended position corresponding to the maximum emptying of the fluid product reservoir located in the emptying position.

13. The applicator according to claim 12, wherein the actuation member acts directly on the fluid product reservoir located in the emptying position through a lateral window of the cylinder.

14. The applicator according to claim 13, wherein the intermediate module comprises actuation means to rotate the cylinder of the cartridge module.

15. The applicator according to claim 13, wherein the application face of the cartridge module is blocked in rotation by the intermediate module, each of the several fluid product reservoirs comprises a removable blocking member which is removed from arrival in the emptying position by an opening member integral with the application face.

* * * * *